(12) United States Patent
Park et al.

(10) Patent No.: US 11,413,010 B2
(45) Date of Patent: Aug. 16, 2022

(54) ULTRASOUND DIAGNOSIS APPARATUS AND METHOD OF OPERATING THE SAME

(71) Applicant: SAMSUNG MEDISON CO., LTD., Hongcheon-gun (KR)

(72) Inventors: Sung-wook Park, Hongcheon-gun (KR); Jin-yong Lee, Hongcheon-gun (KR); Ji-hyun Yoon, Seoul (KR); Sang-eun Lee, Seoul (KR); Hyuk-jae Chang, Seoul (KR); Namsik Chung, Seoul (KR); In-jeong Cho, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 502 days.

(21) Appl. No.: 15/599,603

(22) Filed: May 19, 2017

(65) Prior Publication Data

US 2018/0085090 A1    Mar. 29, 2018

(30) Foreign Application Priority Data

Sep. 27, 2016  (KR) .................. 10-2016-0124242

(51) Int. Cl.
*A61B 8/00*   (2006.01)
*A61B 8/12*   (2006.01)
*A61B 8/08*   (2006.01)

(52) U.S. Cl.
CPC .......... *A61B 8/4245* (2013.01); *A61B 8/0883* (2013.01); *A61B 8/12* (2013.01);
(Continued)

(58) Field of Classification Search
CPC ......... A61B 8/12; A61B 8/4245; A61B 8/429; A61B 34/20; A61B 2034/2065; A61B 8/4461; A61B 5/6852; A61B 8/4281
See application file for complete search history.

(56) References Cited

U.S. PATENT DOCUMENTS

| 7,678,056 B2 | 3/2010 | Wilser et al. |
| 8,460,195 B2 | 6/2013 | Courtney et al. |

(Continued)

FOREIGN PATENT DOCUMENTS

| CN | 203724128 U | 7/2014 |
| JP | 2006-198239 A | 8/2006 |

(Continued)

OTHER PUBLICATIONS

Communication dated Jan. 10, 2018, issued by the European Patent Office in counterpart European application No. 17167794.1.

(Continued)

*Primary Examiner* — Boniface Ngathi N
*Assistant Examiner* — Milton Truong
(74) *Attorney, Agent, or Firm* — Sughrue Mion, PLLC

(57) ABSTRACT

Provided are an ultrasound diagnosis apparatus and a method of operating the same, which are capable of providing a guide for improving quality of an ultrasound image according to a relative position between a transducer and an object. The ultrasound diagnosis apparatus includes: a probe configured to transmit ultrasound signals to an object and receive ultrasound echo signals reflected from the object; a display configured to display a state of contact between the object and the probe; and a processor configured to determine, based on the ultrasound echo signals, whether the probe is brought into contact with the object and the state of contact between the object and the probe, and to control the display to display an indicator indicating a result of the determining.

12 Claims, 18 Drawing Sheets

(52) U.S. Cl.
CPC ............ *A61B 8/429* (2013.01); *A61B 8/4444* (2013.01); *A61B 8/4494* (2013.01); *A61B 8/464* (2013.01); *A61B 8/465* (2013.01); *A61B 8/467* (2013.01); *A61B 8/5207* (2013.01); *A61B 8/54* (2013.01); *A61B 8/461* (2013.01)

(56) References Cited

U.S. PATENT DOCUMENTS

| | | | | |
|---|---|---|---|---|
| 2003/0092994 | A1* | 5/2003 | Miller | A61B 5/6819 600/463 |
| 2008/0177138 | A1* | 7/2008 | Courtney | A61B 5/0062 600/109 |
| 2010/0010348 | A1* | 1/2010 | Halmann | A61B 8/00 600/443 |
| 2010/0160770 | A1* | 6/2010 | Govari | A61B 5/6885 600/424 |
| 2011/0224547 | A1* | 9/2011 | Abe | A61B 8/08 600/443 |
| 2011/0275892 | A1* | 11/2011 | Tanaka | A61B 1/0016 600/109 |
| 2013/0338478 | A1* | 12/2013 | Hirota | A61B 8/429 600/407 |
| 2013/0345715 | A1 | 12/2013 | Gifforod et al. | |
| 2014/0187950 | A1* | 7/2014 | Torp | A61B 8/4254 600/445 |
| 2014/0343426 | A1* | 11/2014 | Kolen | A61B 8/4494 600/440 |
| 2015/0094594 | A1* | 4/2015 | Harhen | A61B 1/00071 600/466 |
| 2015/0182198 | A1* | 7/2015 | Sabourin | A61B 8/14 600/440 |
| 2015/0223782 | A1* | 8/2015 | Yamagata | A61B 8/12 600/462 |
| 2015/0310581 | A1* | 10/2015 | Radulescu | G06T 7/75 348/77 |
| 2015/0320392 | A1 | 11/2015 | Missov et al. | |
| 2016/0150947 | A1 | 6/2016 | Marbor | |
| 2016/0183915 | A1 | 6/2016 | Govari et al. | |
| 2017/0007202 | A1* | 1/2017 | Peszynski | A61B 8/0883 |

FOREIGN PATENT DOCUMENTS

| | | |
|---|---|---|
| JP | 2009-18030 A | 1/2009 |
| WO | 2013/084094 A1 | 6/2013 |
| WO | 2015/166106 A1 | 11/2015 |

OTHER PUBLICATIONS

Communication dated Jul. 2, 2020, from the European Patent Office in European Application No. 17167794.1.

* cited by examiner

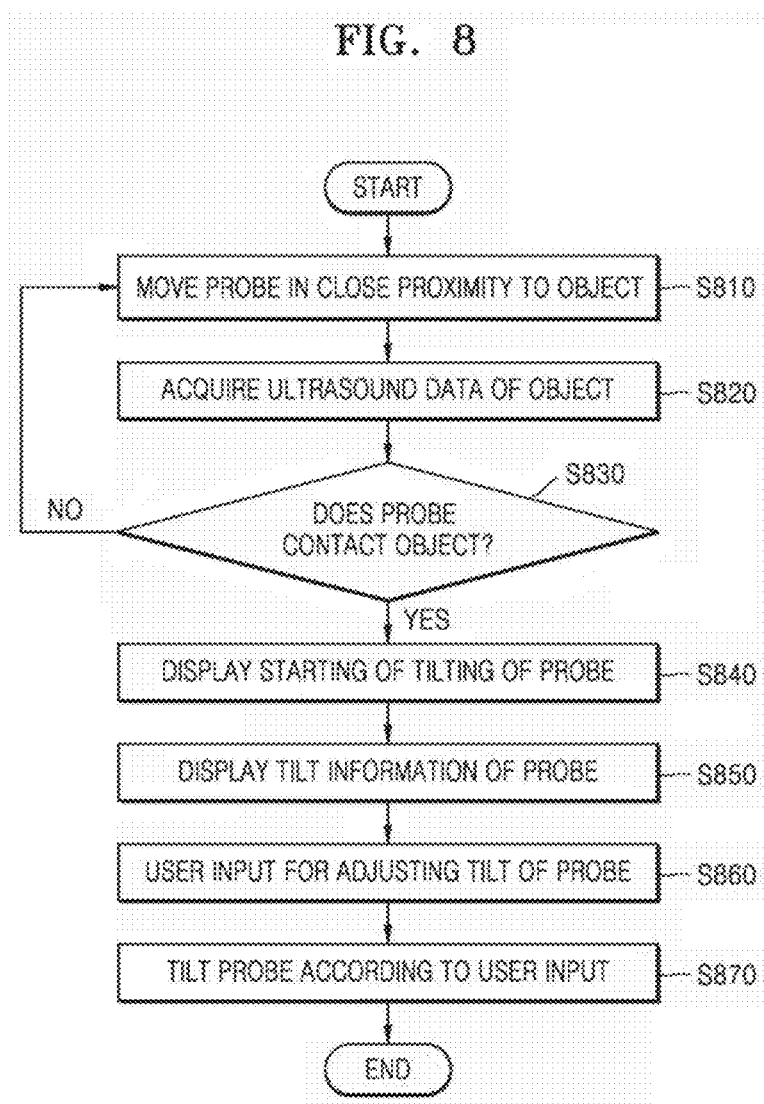

ULTRASOUND DIAGNOSIS APPARATUS AND METHOD OF OPERATING THE SAME

CROSS-REFERENCE TO RELATED APPLICATION

This application claims the benefit of Korean Patent Application No. 10-2016-0124242, filed on Sep. 27, 2016, in the Korean Intellectual Property Office, the disclosure of which is incorporated herein in its entirety by reference.

BACKGROUND

1. Field

The present disclosure relates to ultrasound diagnosis apparatuses and methods of operating the same, and more particularly, to ultrasound diagnosis apparatuses that are capable of providing a guide for improving quality of an ultrasound image according to a relative position between an ultrasonic transducer and an object.

2. Description of the Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

A transesophageal echocardiography (TEE) apparatus is one type of ultrasound diagnosis apparatus that is used to diagnose diseases from inside the human body. TEE is a diagnostic test for recording ultrasound images of heart tissues and may involve transmitting ultrasound waves to the heart, which is an object, and surrounding tissues by passing a long tube with a probe at its distal end down through the esophagus so that the probe is positioned next to the heart and receiving ultrasound echo signals reflected from the object to produce images of the heart chambers, valves, and surrounding structures.

In this case, the tube may be sufficiently rigid but flexible enough to pass down through the esophagus into a desired position. Furthermore, a flexible bending part is positioned between the tube and the probe so that the probe may pass through a curved esophagus and be placed at a suitable position that facilitates diagnosis of diseases of the heart.

SUMMARY

Provided are ultrasound diagnosis apparatuses and methods of operating the same, which are capable of providing a guide for improving quality of an ultrasound image according to a relative position between an ultrasonic transducer and an object.

Additional aspects will be set forth in part in the description which follows and, in part, will be apparent from the description, or may be learned by practice of the presented embodiments.

According to an aspect of an embodiment, an ultrasound diagnosis apparatus includes: a probe configured to transmit ultrasound signals to an object and receive ultrasound echo signals reflected from the object; a display configured to display a state of contact between the object and the probe; and a processor configured to determine, based on the ultrasound echo signals, whether the probe is brought into contact with the object and the state of contact between the object and the probe, and to control the display to display an indicator indicating a result of the determining.

The probe may be tilted at a specific angle with respect to the object.

A first indicator may indicate that tilting of the probe is about to start according to the result of the determining.

A second indicator may indicate tilt information of the probe according to the state of contact between the object and the probe.

The ultrasound diagnosis apparatus may further include an input interface configured to receive a user input for adjusting a tilt of the probe according to the second indicator, and the probe may be tilted according to the received user input.

The display is further configured to include at least one of a display device, an audio device, and a vibration device equipped with haptic functions.

An indication that the tilting of the probe is about to start may be transmitted via at least one of an image, a text, a voice, and a vibration.

The tilt information of the probe may be transmitted via at least one of an image, a text, and a voice.

The processor is further configured to tilt the probe at a specific angle and control the probe to repeat an operation of transmitting the ultrasound signals respectively at positions to which the probe is tilted and receiving the ultrasound echo signals reflected from the object.

The probe may be positioned at a distal end of the ultrasound diagnosis apparatus and may be a transesophageal echocardiography (TEE) probe for insertion into a body cavity, and the ultrasound diagnosis apparatus may further include a neck assembly that is connected to the probe and bent.

According to an aspect of another embodiment, a method of operating an ultrasound diagnosis apparatus includes: moving a probe in close proximity to an object; acquiring ultrasound data of the object; determining whether the probe is brought into contact with the object based on the acquired ultrasound data; and tilting the object according to a result of the determining.

The method may further include displaying, when the probe is brought into contact with the object, an indication that tilting of the probe is about to start.

The method may further include: displaying tilt information of the probe according to a state in which the probe is brought into contact with the object; and entering a user input for adjusting a tilt of the probe according to the displayed tilt information of the probe.

The indication that the tilting of the probe is about to start may be transmitted via at least one of an image, a text, a voice, and a vibration.

The tilt information of the probe may be transmitted via at least one of an image, a text, and a voice.

According to an aspect of another embodiment, a method of operating an ultrasound diagnosis apparatus includes: moving a probe in close proximity to an object; repeatedly tilting the probe; acquiring ultrasound data of the object respectively at positions to which the probe is tilted; and comparing the acquired ultrasound data with one another.

A relative position of the probe with respect to the object may be determined at a tilt position where a region with respect to which the ultrasound data is acquired has a largest area.

When the ultrasound diagnosis apparatus includes a TEE probe for insertion into a body cavity as the probe, the moving of the probe in close proximity to the object may include inserting the probe into the body cavity and bending a neck assembly connected to the probe positioned at a distal end of the ultrasound diagnosis apparatus.

BRIEF DESCRIPTION OF THE DRAWINGS

These and/or other aspects will become apparent and more readily appreciated from the following description of the embodiments, taken in conjunction with the accompanying drawings, in which reference numerals denote structural elements:

FIG. 8 is a flowchart of a method of operating an ultrasound diagnosis apparatus according to an embodiment;

DETAILED DESCRIPTION

Figure 1:
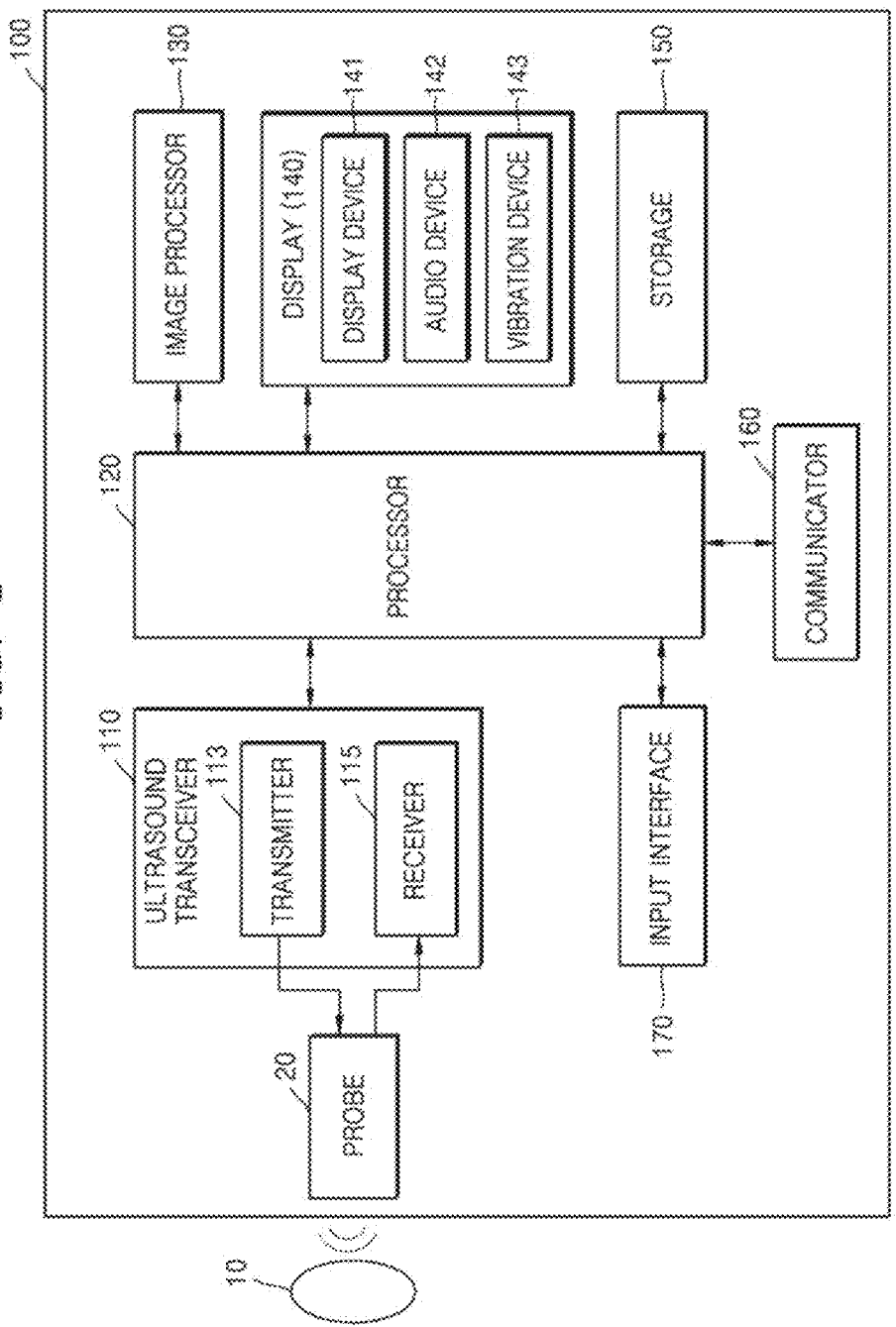
FIG. 1 is a block diagram illustrating a configuration of an ultrasound diagnosis apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an "ultrasound image" refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a processor 120, an image processor 130, a display 140, a storage 150, e.g., a memory, a communicator 160, i.e., a communication device or an interface, and an input interface 170.

In the present embodiment, the probe 20 may include a plurality of transducers. The transducers are arranged in two dimensions (2D), forming a 2D transducer array.

For example, the 2D transducer array may include a plurality of sub-arrays arranged in a first direction, each of the sub-arrays including a plurality of transducers arranged in a second direction that is different from the first direction.

The ultrasound transceiver 110 may include an analog beamformer 113 and a digital beamformer 115. Although FIG. 1 illustrates that the ultrasound transceiver 110 and the probe 20 are provided as being separate from each other, the probe 20 according to the present exemplary embodiment may include the entire ultrasound transceiver 110 or a part of the ultrasound transceiver 110. For example, the probe 20 may include one or both of the analog beamformer 113 and the digital beamformer 115.

The processor 120 may calculate a time delay value for digital beamforming with respect to the sub-arrays included in the 2D transducer array. Also, the processor 120 may calculate a time delay value for analog beamforming for each of the transducers included in any one sub-array of the sub-arrays.

The processor 120 may control the analog beamformer 113 and the digital beamformer 115 to form a transmission signal to be applied to each of the transducers, according to the time delay values for analog beamforming and digital beamforming.

Also, the processor 120 may control the analog beamformer 113 to add signals received from the transducers for each sub-array, according to the time delay value for analog beamforming. Also, the processor 120 may control the ultrasound transceiver 110 to perform analog to digital conversion of the signals added for each sub-array. Also, the processor 120 may control the digital beamformer 115 to generate ultrasound data by adding the digitized signals according to the time delay value for digital beamforming.

Also, the processor 120 may control the analog beamformer 113 to classify the transducers to be included in the sub-arrays, apply the time delay value for performing analog beamforming, and add the signals for each of the sub-arrays. Also, the processor 120 may control the analog beamformer 113 to add again synthesized signals generated by adding the signals for each sub-array by applying the time delay value for performing analog beamforming.

The image processor 130 generates an ultrasound image by using generated ultrasound data.

The display 140 may display a generated ultrasound image and various pieces of information processed by the ultrasound diagnosis apparatus 100. The display 140 may include one or more display devices 141, an audio device 142, or a vibration device 143, according to its implemented configuration. In this case, the one or more display devices 141 may be combined with a touch panel to form a touch screen.

The processor 120 may control the operations of the ultrasound diagnosis apparatus 100 and flow of signals between the internal elements of the ultrasound diagnosis apparatus 100. The processor 120 may include a memory for storing a program or data to perform functions of the ultrasound diagnosis apparatus 100 and a processor and/or a microprocessor (not shown) for processing the program or data. For example, the processor 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the processor 120 so that the processor 120 may control the ultrasound diagnosis apparatus 100 in response to the received control signal.

The processor 120 may transmit a control signal to the external apparatus via the communicator 160 so that the external apparatus may be controlled in response to the control signal of the processor 120.

For example, the external apparatus connected to the ultrasound diagnosis apparatus 100 may process the data of the external apparatus in response to the control signal of the processor 120 received via the communicator 160.

A program for controlling the ultrasound diagnosis apparatus 100 may be installed in the external apparatus. The program may include command languages to perform part of operation of the processor 120 or the entire operation of the processor 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2C:
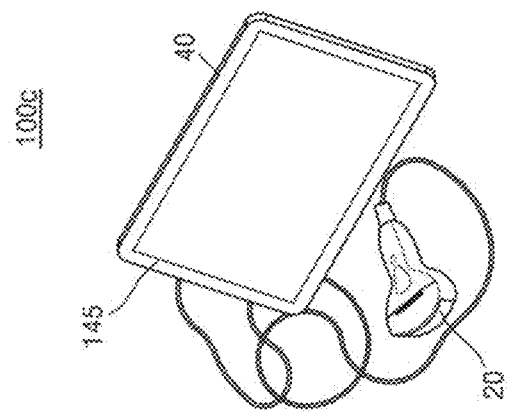
FIGS. 2A, 2B, and 2C are diagrams illustrating ultrasound diagnosis apparatus according to an exemplary embodiment.
Figure 2B:
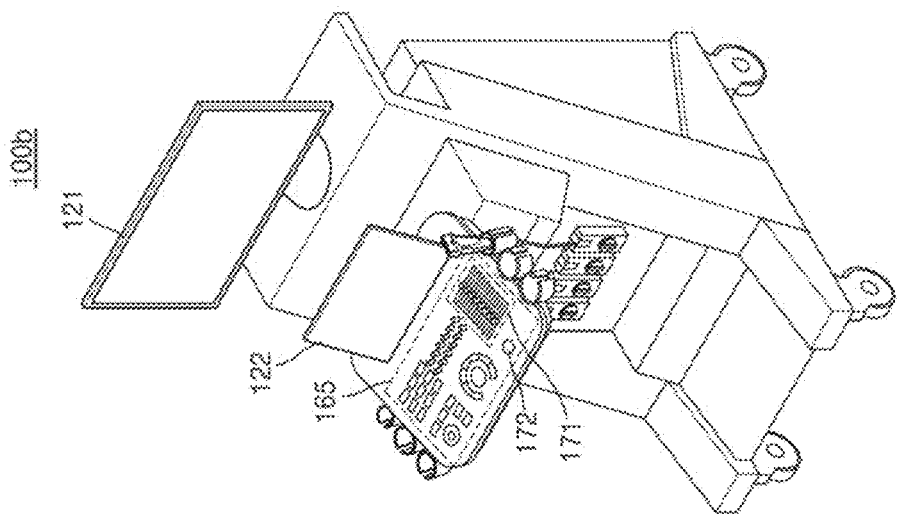
Figure 2A:
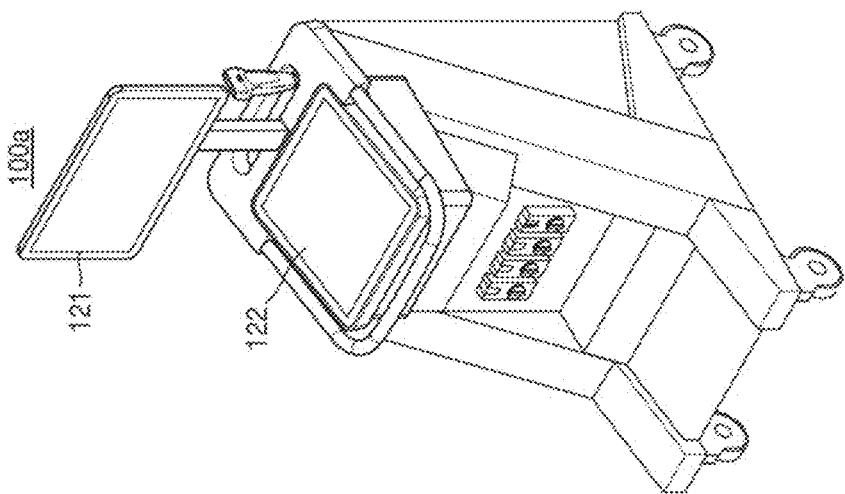

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Hereinafter, embodiments of the present disclosure will be described more fully with reference to the accompanying drawings. While it is assumed hereinafter that a transesophageal echocardiography (TEE) apparatus is used as the ultrasound diagnosis apparatus 100, embodiments are not limited to the field of TEE, and may be applied to any one of ultrasound diagnosis apparatuses.

Figure 3:
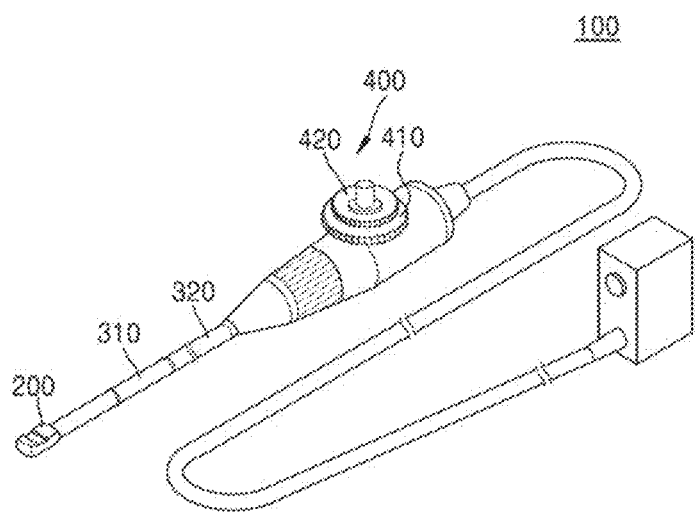
FIG. 3 is a perspective view of an ultrasound diagnosis apparatus according to an embodiment.
Figure 4:
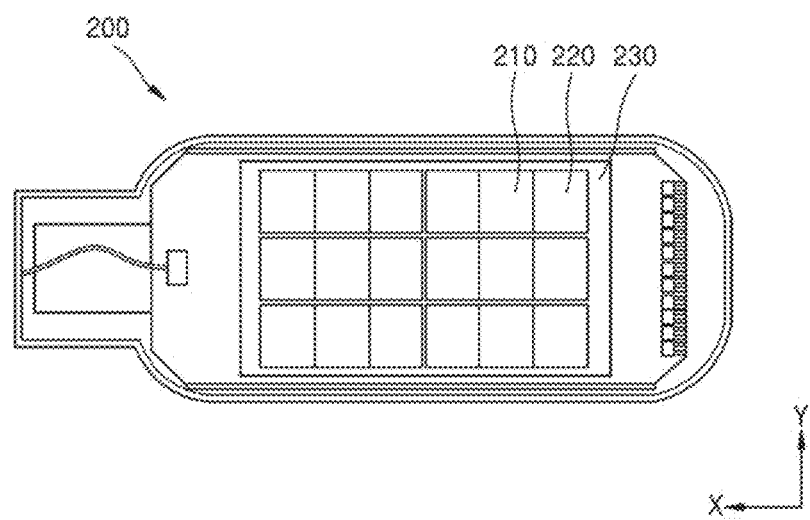
FIG. 4 is a cross-sectional view of a probe according to an embodiment.

FIG. 3 is a perspective view of an ultrasound diagnosis apparatus 100 according to an embodiment, and FIG. 4 is a cross-sectional view of a probe 200 according to an embodiment.

Referring to FIGS. 3 and 4, the ultrasound diagnosis apparatus 100 according to the present embodiment may mainly include the probe 200, a neck assembly 310, an insertion tube 320, and a manipulator 400. The probe 200 is configured to emit ultrasound waves toward an object and receive ultrasound echo signals reflected from the object in order to obtain an image of an internal area of the object. As shown in FIG. 4, the probe 200 may include an ultrasonic transducer 210, an integrated circuit (IC) 220, and a base 230.

According to an embodiment, the ultrasonic transducer 210 generates ultrasonic waves by converting electrical signals supplied from the outside into mechanical vibration energy and converts vibrations transmitted from the outside back into electrical signals. In the present embodiment, a capacitive micromachined ultrasonic transducer (cMUT) may be used as the ultrasonic transducer 210. However, embodiments are not limited thereto, and a piezo-electric transducer (PZT) may be used as the ultrasonic transducer 210. Furthermore, the ultrasonic transducer 210 may have a two-dimensional (2D) array structure as shown in FIG. 4, but embodiments are not limited thereto.

The IC 220 is configured to generate an ultrasound signal by applying an electrical signal to the ultrasonic transducer 210 to drive the ultrasonic transducer 210 and to detect an electrical signal output from the ultrasonic transducer 210 by using the ultrasound signal transmitted to the ultrasonic transducer 210 from the outside. The IC 220 has two opposite surfaces, and the ultrasonic transducer 210 may be provided on one surface thereof. As described above, the ultrasonic transducer 210 may be mounted onto the one surface of the IC 220 via flip-chip bonding, but embodiments are not limited thereto.

The base 230 is a support member for supporting the ultrasonic transducer 210. For example, a printed circuit board (PCB; not shown) may be provided on one surface of the base 230. In this case, the PCB may be electrically connected to the IC 220 via wire bonding. However, embodiments are not limited thereto, and the PCB and the IC 220 may be electrically connected to each other by using various other methods.

The neck assembly 310 may be a bendable articulation mechanism and be arranged between the probe 200 and the insertion tube 320. In other words, the neck assembly 310 may be configured to facilitate insertion of the probe 200 into a curved esophagus and placement of the probe 200 at a desired position for diagnosis. For example, the neck assembly 310 may include a plurality of segments and a manipulating wire for connecting the plurality of segments to each other. The neck assembly 310 with the plurality of segments joined together is formed to have a cylindrical shape with a hollow portion so as to accommodate cables for propagation of signals that are transmitted from the ultrasound transceiver 110 of FIG. 1 to the probe 200 or vice versa. Furthermore, the neck assembly 310 may be made of a metal, but embodiments are not limited thereto. The neck assembly 310 may be formed of any material having a good thermal conductivity and a specific strength. An outer wall of the neck assembly 310 may be coated with a highly elastic material. The movement of the probe 200 via the neck assembly 310 will be described in more detail below with reference to FIGS. 7A and 7B.

The insertion tube 320 may have one end coupled to the neck assembly 310 and the other end coupled to the manipulator 400. The insertion tube 320 may have sufficient flexibility to easily pass down through the esophagus and sufficient rigidity to prevent damage during its insertion. Furthermore, the insertion tube 320 may generally have a length of about 100 cm to about 110 cm and a diameter of about 10 F mm to about 20 F mm, but embodiments are not limited thereto.

The manipulator 400 manipulates an operation of the probe 200, and may include a first knob for moving the probe 200 left or right and a second knob 420 for moving the probe 200 up or down, but embodiments are not limited thereto.

Figure 5A:
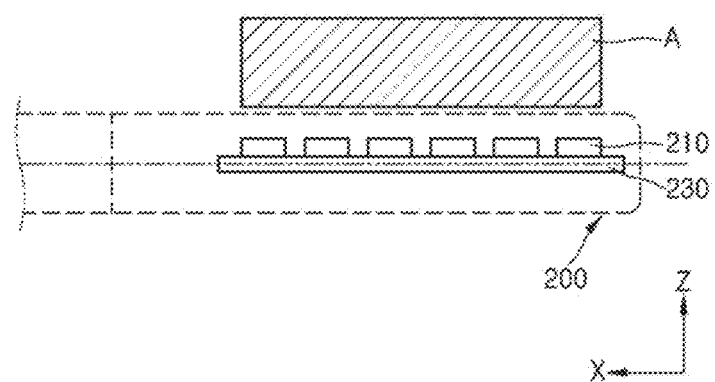
FIGS. 5A through 5C are schematic side cross-sectional views of a probe according to an embodiment.
Figure 5B:
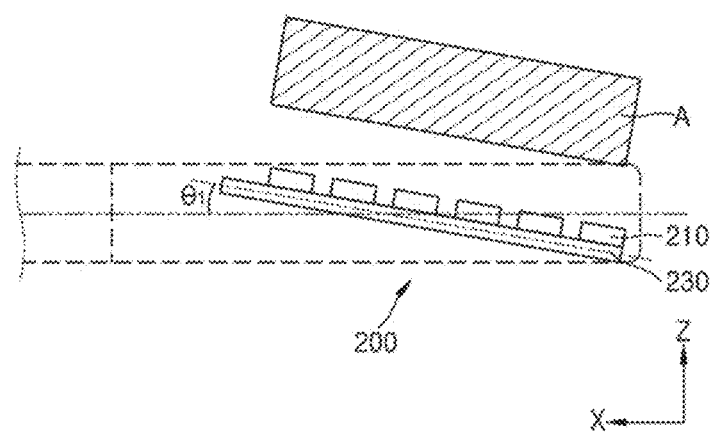
Figure 5C:
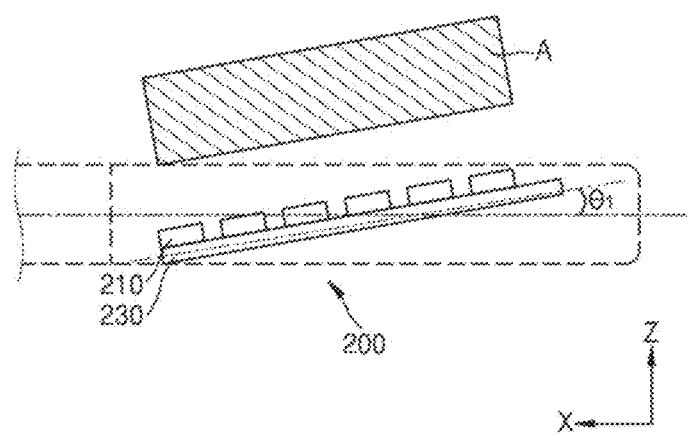
Figure 6A:
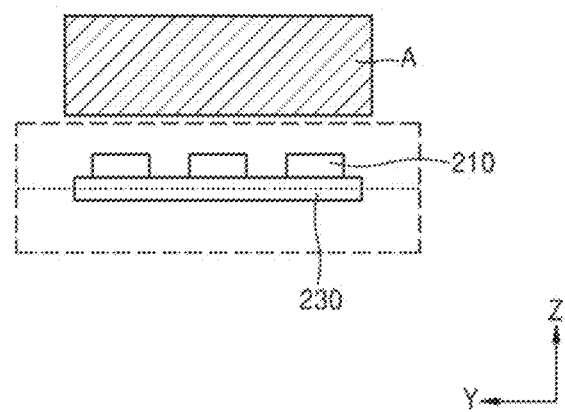
FIGS. 6A through 6C are schematic side cross-sectional views of a probe according to an embodiment.
Figure 6B:
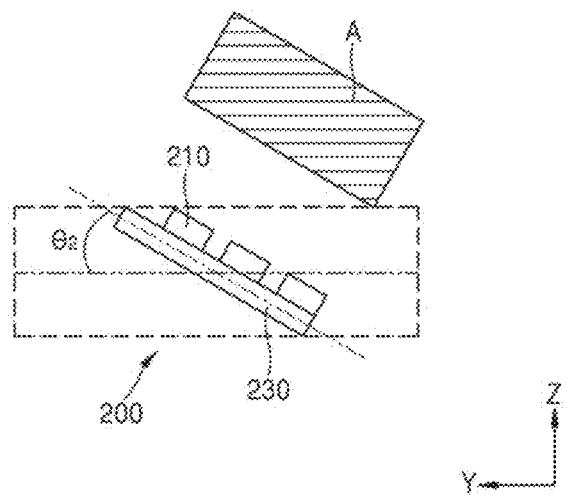
Figure 6C:
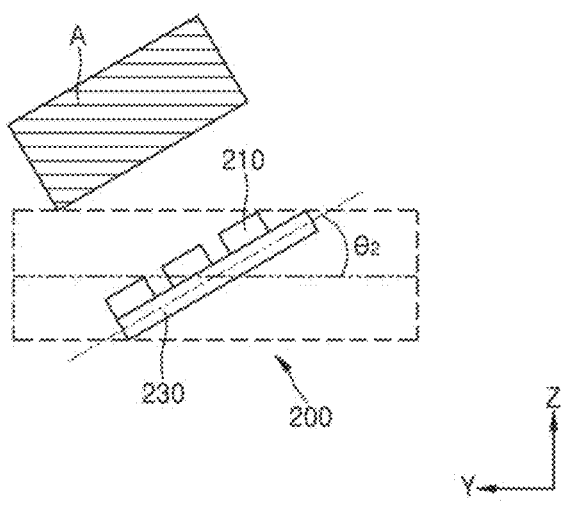

FIGS. 5A through 5C are schematic side cross-sectional views of a probe 200 according to an embodiment, and FIGS. 6A through 6C are schematic side cross-sectional views of a probe 200 according to an embodiment.

Referring to FIG. 5A, when the probe 200 is brought into close contact with an object A, the ultrasonic transducer 210 may be arranged perpendicular to a direction of emission of ultrasound waves opposite to the object A. In other words, the ultrasonic transducer 210 may be mounted on one surface of a base 230 and arranged along a first axis (X) direction perpendicular to a third Z axis direction that is the direction of emission of ultrasound waves. As describe above, when the probe 200 is brought into close contact with the object A so that the ultrasonic transducer 210 may oppose the object A, it is possible to acquire a relatively clear image via the ultrasonic transducer 210. Otherwise, if the probe 200 and the object A are not brought into close contact with each other, the ultrasonic transducer 210 needs to be tilted to form a specific angle with respect to the first X axis direction in order to obtain a clearer image.

According to an embodiment, referring to FIG. 5B, when the probe 200 and the object A are not brought into close contact with each other, the base 230 where the ultrasonic transducer 210 is mounted may be tilted along a clockwise direction relative to the first X axis, so that the object A and the ultrasonic transducer 210 are opposite to each other. In this case, the base 230 may be tilted to form a first angle $\theta_1$ with respect to the first X axis. Furthermore, referring to FIG. 5C, the base 230 where the ultrasonic transducer 210 is mounted may be tilted along a counter-clockwise direction relative to the first X axis. In this case, the base 230 may be tilted to form the first angle $\theta_1$ with respect to the first X axis. For example, the first angle $\theta_1$ may be less than or equal to 15°, but embodiments are not limited thereto.

Furthermore, the ultrasonic transducer 210 may be tilted to form a second angle $\theta_2$ with respect to a second Y axis according to a state of contact between the ultrasonic transducer 210 and the object A. According to an embodiment, referring to FIGS. 6A through 6C, the ultrasonic transducer 210 mounted on one surface of the base 230 may be arranged along the second Y axis that is perpendicular to the third Z axis extending in the direction of emission of ultrasound waves. If the probe 200 and the object A are brought into close contact with each other, the base 230 may not be tilted relative to the second Y axis. Otherwise, if the probe 200 and the object A are not brought into close contact with each other, the base 230 where the ultrasonic transducer 210 is mounted may be tilted to form the second angle $\theta_2$ with respect to the second Y axis along a clockwise or counter-clockwise direction. For example, the second angle $\theta_2$ may be less than or equal to 15°, but embodiments are not limited thereto. Although not shown in FIGS. 6A and 6B, the ultrasonic transducer 210 may rotate about the third Z axis in the clockwise or counter-clockwise direction in order to obtain a clearer image according to a state of contact between the ultrasonic transducer 210 and the object A.

Figure 7A:
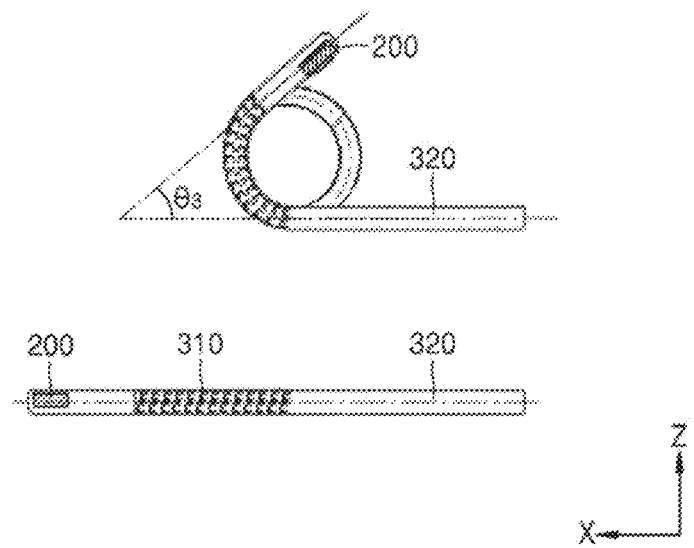
FIGS. 7A and 7B are schematic side views of an ultrasound diagnosis apparatus according to an embodiment.
Figure 7B:
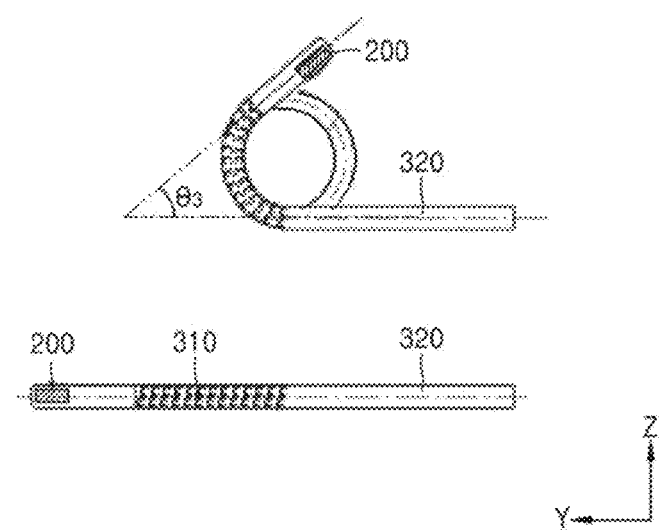

FIGS. 7A and 7B are schematic side views of the ultrasound diagnosis apparatus 100 according to an embodiment.

As described above, according to an embodiment, the ultrasound diagnosis apparatus 100 may include a probe 200 for performing TEE diagnosis in a curved esophagus within a body cavity. Referring to FIGS. 7A and 7B, the ultrasound diagnosis apparatus 100 may further include a neck assembly 310 provided between the probe 200 and an insertion tube 320. The neck assembly 310 may be bent at a third angle $\theta_3$ along one direction in order to insert the probe 200 into a curved esophagus. In this case, the third angle $\theta_3$ may be in a range of between −180° and +180°. Thus, the neck assembly 310 may be bent to the extent of forming a U shape in a clockwise or counter-clockwise direction. In other words, the neck assembly 310 may be bent at 360° in a XZ plane as shown in FIG. 7A and a YZ plane as shown in FIG. 7B.

FIG. 8 is a flowchart of a method of operating the ultrasound diagnosis apparatus 100 according to an embodiment.

Figure 9A:
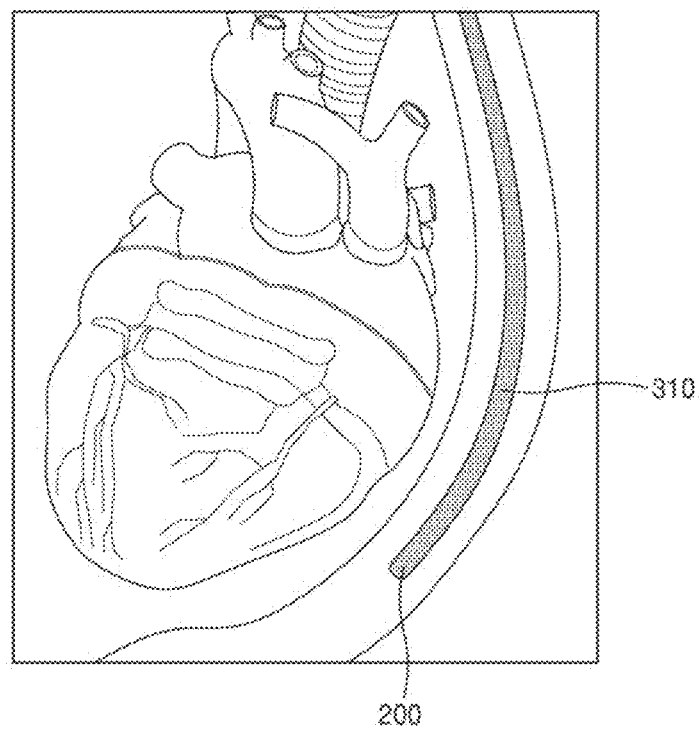
FIGS. 9A and 9B are schematic diagrams illustrating a diagnosis performed using an ultrasound diagnosis apparatus according to an embodiment.
Figure 9B:
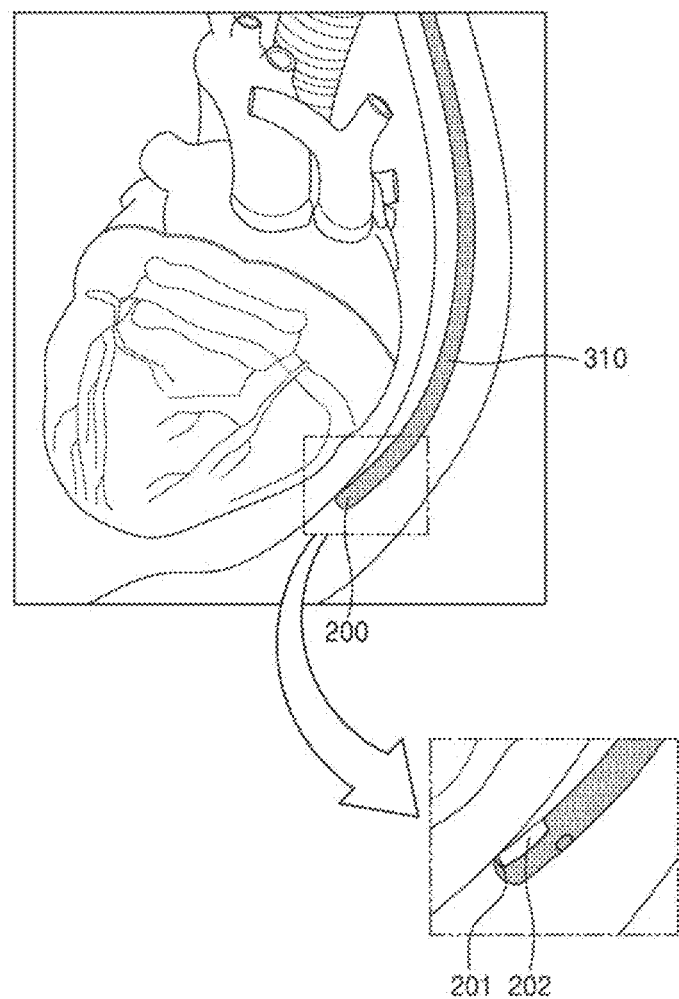

Referring to FIG. 8, the probe 200 of the ultrasound diagnosis apparatus 100 is moved in close proximity to an object (S810). According to an embodiment, when the ultrasound diagnosis apparatus 100 includes a TEE probe for insertion into a body cavity of the object, the probe 200 may be inserted into the body cavity of the object as shown in FIG. 9A. In this case, the probe 200 may be separated from the heart being imaged for ultrasound diagnosis. To minimize a separation distance between the probe 200 and the heart, the neck assembly 310 may be bent as shown in FIG. 9B. For example, as shown in FIGS. 7A and 7B, the neck assembly 310 may be bent up, down, left, or right so that the probe 200 at a distal end of the ultrasound diagnosis apparatus 100 may be moved to a position closest to the heart.

The ultrasound diagnosis apparatus 100 acquires ultrasound data of the object (S820). In this case, the ultrasound data may be acquired using the probe 200 included in the ultrasound diagnosis apparatus 100 or may be received from an external device. According to an embodiment, when the ultrasound data is acquired using the probe 200, the ultrasound data is acquired by transmitting ultrasound signals from the probe 200 to the object and receiving ultrasound echo signals reflected from the object. However, the ultrasound signals transmitted by the probe 200 may not be reflected from the object according to a state of contact between the probe 200 and the object. In this case, the ultrasound data corresponding to these ultrasound signals may not be acquired.

According to an embodiment, depending on a position into which the probe 200 is passed and a shape of the object, as shown in FIG. 9B, a portion 201 of the probe 200 may contact the object while the remaining portion 202 thereof may not contact the object. In this case, ultrasound signals transmitted from the portion 201 of the probe 200 that contacts the object may be received by the receiver (115 of FIG. 1) while ultrasound signals transmitted from the remaining portion 202 may not be received thereby. When ultrasound data is acquired based on ultrasound signals received only from the portion 201 of the probe 200 as described above, an ultrasound image is generated based on only the acquired ultrasound data.

Figure 10A:
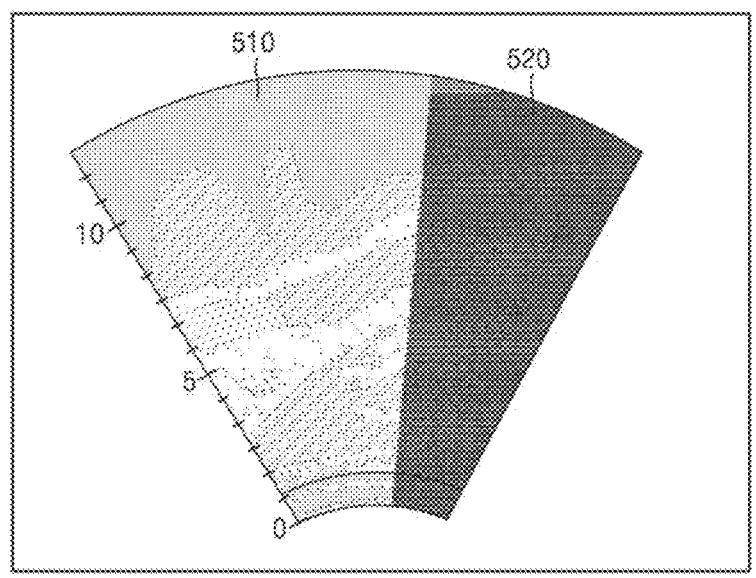
FIGS. 10A and 10B illustrate ultrasound images generated using an ultrasound diagnosis apparatus according to an embodiment.
Figure 10B:
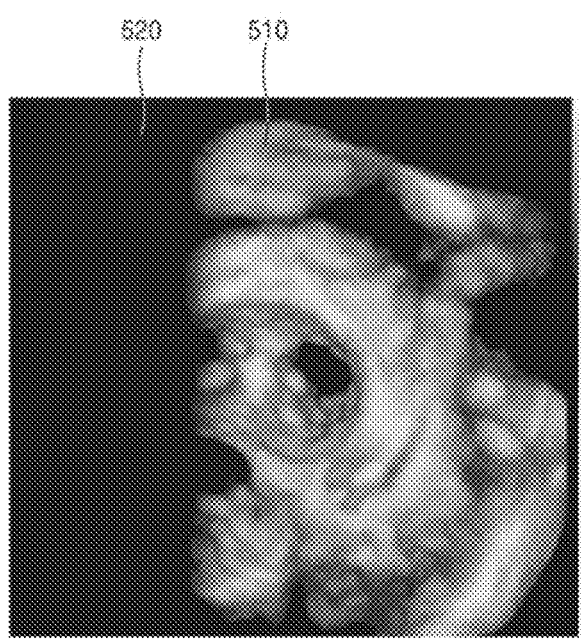

According to an embodiment, a 2D ultrasound image as shown in FIG. 10A or a three-dimensional (3D) ultrasound image of a sample volume as shown in FIG. 10B may be displayed on the display device (141 of FIG. 1). In this case, the 2D or 3D ultrasound image may be separated into a first region 510 with respect to which ultrasound data is acquired and a second region 520 with respect to which ultrasound data is not acquired. According to an embodiment, the second region 520 may be indicated in a mono-color such as white or black, but embodiments are not limited thereto. Furthermore, ultrasound images may be displayed on the display device 141 in a plurality of modes for providing an ultrasound image (hereinafter, referred to as a 'composite mode'). The composite mode may include a brightness (B)-mode for providing a B-mode image, a Color Doppler mode (C-mode) or a Power Doppler mode (P-mode) for providing a color flow image, and a Doppler mode (D-mode) for providing a Doppler spectrum.

The ultrasound diagnosis apparatus 100 determines whether the object and the probe 200 are brought into contact with each other (S830). As described above, according to whether the probe 200 and the object contact each other, ultrasound signals transmitted from the probe 200 may not be reflected from the object, and thus, ultrasound data corresponding to the ultrasound signals may not be acquired. In this case, by analyzing ultrasound signals reflected from the object and received by the receiver 115 and those not received by the received 115, the ultrasound diagnosis apparatus 100 may determine a state of contact between the probe 200 and the object. For example, if the probe 200 is completely separated from the object as shown in FIG. 9A, a very small number of ultrasound signals may be reflected from the object and received. Otherwise, if the probe 200 is brought into contact with the object as shown in FIG. 9B, a large number of ultrasound signals transmitted from the probe 200 may be reflected from the object and received.

The state of contact between the object and the probe 200 may be determined according to the number of ultrasound signals reflected from the object and received. According to an embodiment, as shown in FIGS. 10A and 10B, the state of contact between the object and the probe 200 may be determined based on a ratio between the first region 510 with respect to which ultrasound data is acquired to the second region 520 with respect to which ultrasound data is not acquired. For example, if a ratio of the first region 510 compared to a whole region exceeds a specific range, the processor (120 of FIG. 1) may determine that the object and the probe 200 are brought into contact with each other. In this case, a criterion for determining whether the object and the probe 200 are brought into contact with each other may be previously input via the storage (150 of FIG. 1) or may be received from a user via the input interface (170 of FIG. 1).

The ultrasound diagnosis apparatus 100 displays starting of tilting of the probe 200 (S840). When the object and the probe 200 contact each other, the starting of tilting of the probe 200 is displayed on the display (140 of FIG. 1). If the object has a curved shape, or if the probe 200 is inserted into a body cavity so that the user is unable to directly manipulate the probe, the probe 200 may not be brought into complete contact with the object. Thus, even when the probe 200 and the object contact each other, as shown in FIGS. 10A and 10B, the ultrasound image may be of the second region 520 with respect to which ultrasound data is not acquired. To minimize the second region 520, the probe 200 may be tilted as shown in FIGS. 5A through 5C and FIGS. 6A through 6C.

Figure 11:
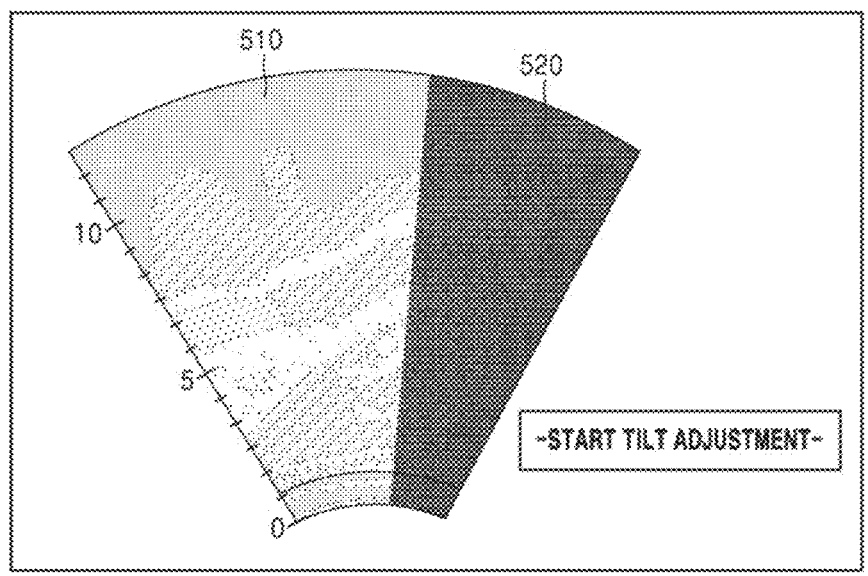
FIG. 11 illustrates an ultrasound image and a first indicator displayed therewith, according to an embodiment.

Tilting of the probe 200 may be performed after contact between the probe 200 and the object occurs, and accordingly, an indicator indicating start of the tilting of the probe 200 may be displayed According to an embodiment, the starting of tilting of the probe 200 may be indicated by a first indicator as shown in FIG. 11. For example, a visual indicator indicating that tilting of the probe 200 is about to start may be displayed on the display device 141 as a text, together with an ultrasound image. Furthermore, a visual indicator that indicates a state of contact between the probe 200 and the object may be displayed on the display device 141 as an image, together with an ultrasound image. According to an embodiment, the starting of tilting of the probe 200 may be indicated by outputting an audio indicator indicating that tilting of the probe 200 is to start via the audio device (142 of FIG. 1) (e.g., a speaker). In addition, according to an embodiment, the starting of tilting of the probe 200 may be indicated by outputting a vibration indicator, which indicates that tilting of the probe 200 is to start, via the vibration device (143 of FIG. 1) equipped with a corresponding haptic function.

The ultrasound diagnosis apparatus 100 displays tilt information of the probe 200 (S850). When the starting of tilting of the probe 200 is displayed, the ultrasound diagnosis apparatus 100 may provide the user with the tilt information of the probe 200. According to an embodiment, in order to provide the user with the tilt information of the probe 200, information about an ultrasound image, corresponding to a state of contact between the probe 200 and the object, may be prestored in the storage 150.

Figure 12A:
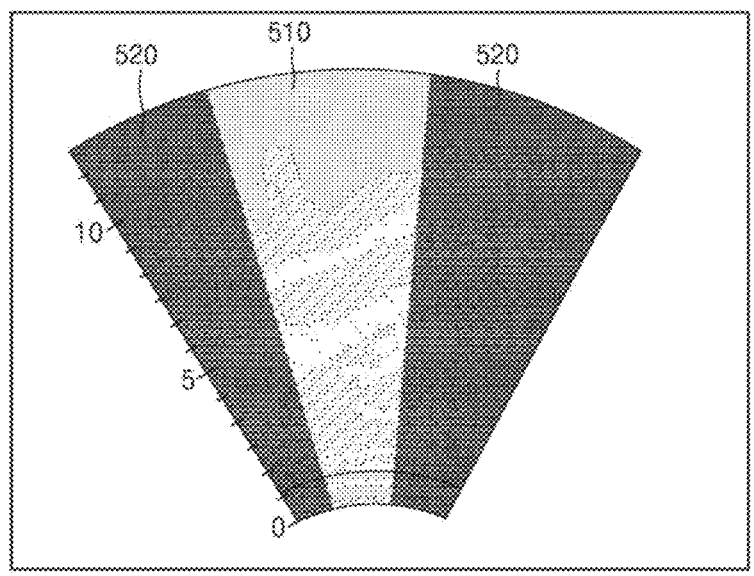
FIG. 12A illustrates an ultrasound image according to an embodiment.
Figure 12B:
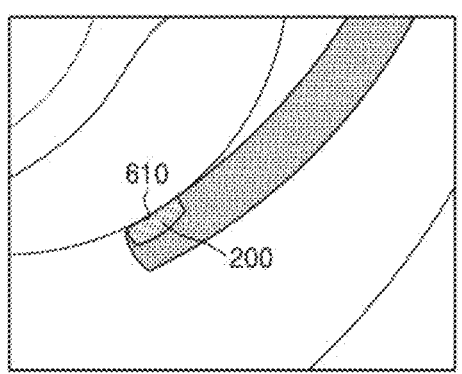
FIG. 12B is a schematic diagram illustrating a diagnosis during which the ultrasound image of FIG. 12A is obtained.
Figure 12C:
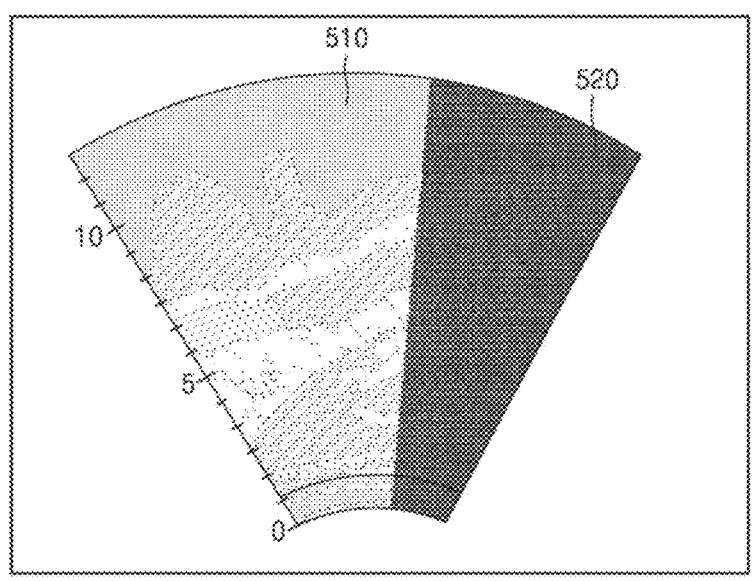
FIG. 12C illustrates an ultrasound image according to an embodiment.
Figure 12D:
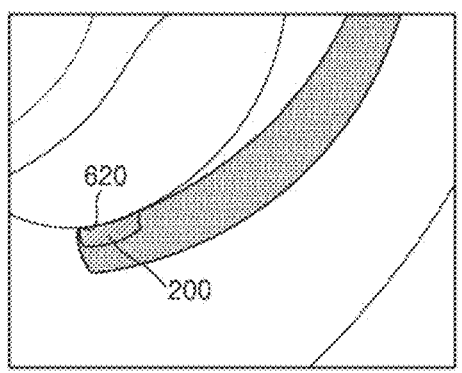
FIG. 12D is a schematic diagram illustrating a diagnosis during which the ultrasound image of FIG. 12C is obtained.
Figure 12E:
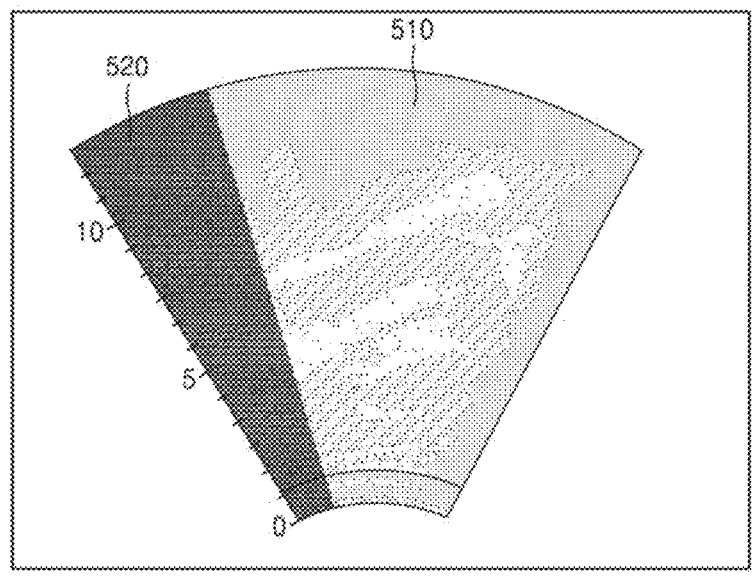
FIG. 12E illustrates an ultrasound image according to an embodiment.
Figure 12F:
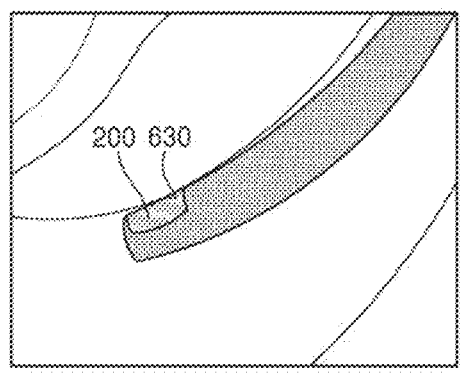
FIG. 12F is a schematic diagram illustrating a diagnosis during which the ultrasound image of FIG. 12E is obtained.

For example, referring to FIGS. 12A and 12B, if a first portion 610 of the probe 200 contacts the object as shown in FIG. 12B, an ultrasound image shown in FIG. 12A may be stored in the storage 150. Referring to FIGS. 12C and 12D, if a second portion 620 of the probe 200, which is wider than the first portion 610, contacts the object as shown in FIG. 12D, an ultrasound image shown in FIG. 12C may be stored in the storage 150. Referring to FIGS. 12E and 12F, if a third portion 630 of the probe 200 that is at a different position than the second portion 620 contacts the object as shown in FIG. 12F, an ultrasound image shown in FIG. 12E may be stored in the storage 150. In this case, a first region 510 with respect to which ultrasound data is acquired and a second region 520 with respect to which ultrasound data is not acquired may be indicated on each of the ultrasound images shown in FIGS. 12A, 12C, and 12E. Since the first region 510 and the second region 520 are distinguished from each other according to a state of contact between the probe 200 and the object, the states of contact between the probe 200 and the object may respectively correspond to the ultrasound images, each including the first region 510 and the second region 520.

Figure 13:
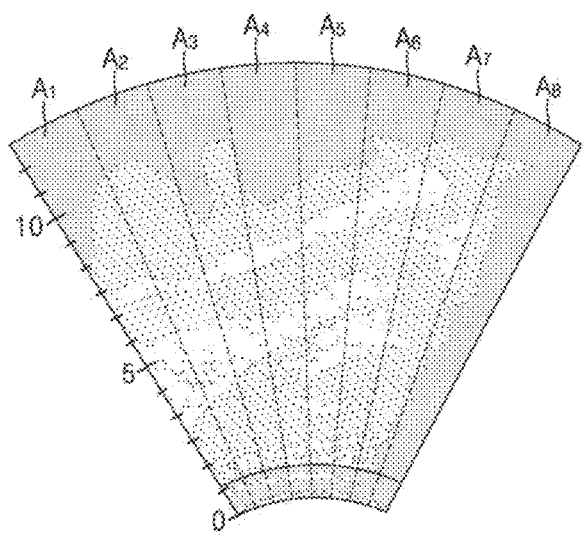
FIG. 13 illustrates an ultrasound image having scan lines indicated thereon according to an embodiment.

As described above, by repeating a process of matching an ultrasound image to a state of contact between the probe 200 and the object, states in which the probe 200 and the object are brought into contact with each other may respectively be standardized according to positions of the first region 510 with respect to which ultrasound data is acquired and the second region 520 with respect to which ultrasound data is not acquired, and may be then stored. For example, as shown in FIG. 13, an ultrasound image may be divided into a plurality of regions $A_1$ through $A_n$ based on a scan line, and states in which the probe 200 and the object are brought into contact with each other may respectively be standardized according to whether each of the regions $A_1$ through $A_n$ is recognized as the first or second region 510 or 520.

A portion of the probe 200 that is in contact with the object and a corresponding ultrasound image may be stored in the storage 150. Thus, when an actual ultrasound image having the first region 510 and the second region 520 is obtained by using actual ultrasound data of the object, the processor 120 may compare the actual ultrasound image with a standardized ultrasound image stored in the storage 150. The processor 120 may determine, according to a comparison result, a state of contact between the object and the probe 200 from which the actual ultrasound image is obtained. After determining the state of contact therebetween, the processor 120 may display tilt information of the probe 200 to the user.

Figure 14:
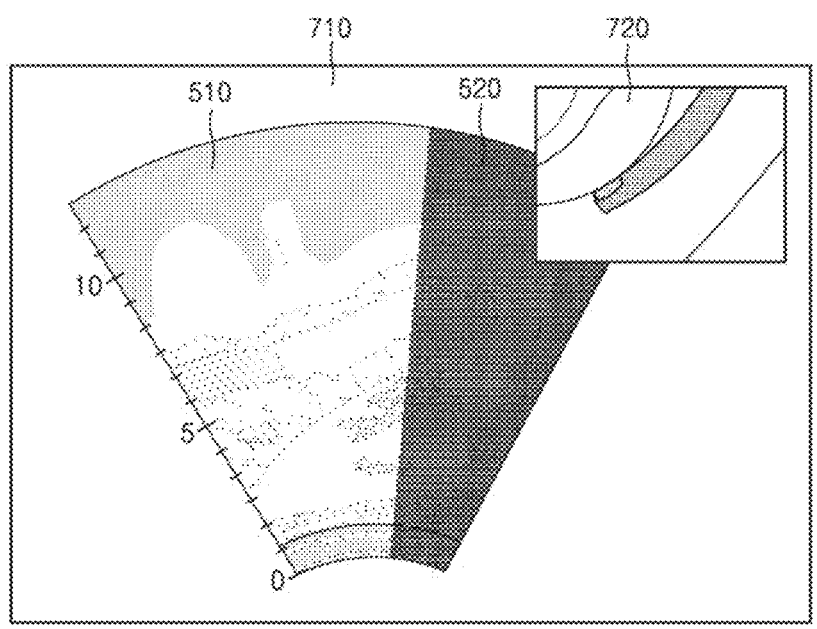
FIGS. 14 and 15 illustrate ultrasound images and second indicators displayed together therewith.
Figure 15:
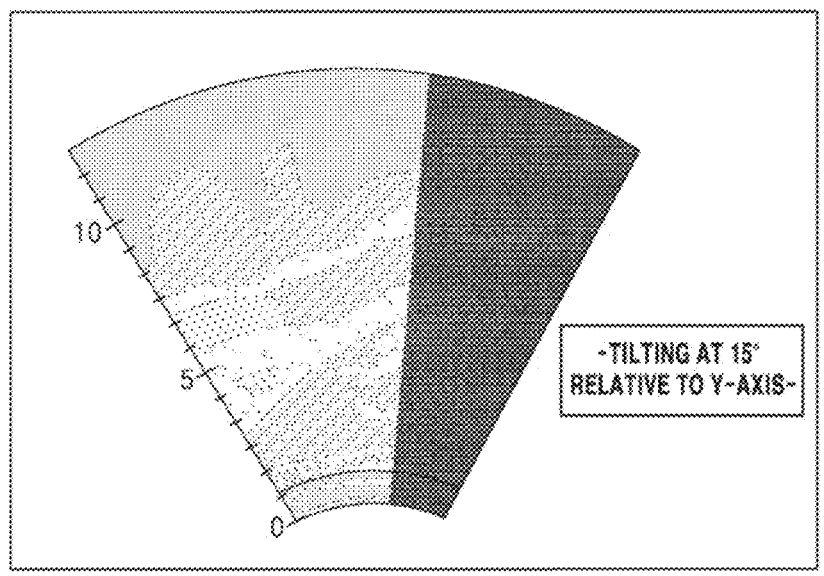

According to an embodiment, tilting information of the probe 200 may be displayed via a second indicator. For example, referring to FIG. 14, an ultrasound image is displayed on a first screen 710 on the display device 141 while a state of contact between the probe 200 and the object is simultaneously being displayed on a second screen 720. After checking the state of contact between the probe 200 and the object displayed on the second screen 720, the user may determine a tilt amount of the probe 200. Furthermore, according to an embodiment, referring to FIG. 15, a visual indicator that directly informs the user of tilting information of the probe 200 may be displayed on the display device 141 as a text. In addition, according to an embodiment, tilting information of the probe 200 may be displayed by outputting an audio indicator indicating a tilt amount of the probe 200 via the audio device 142 (e.g., a speaker).

The user enters a user input for adjusting a tilt of the probe 200 according to the tilt information of the probe 200 provided by the ultrasound diagnosis apparatus 100 (S860). According to an embodiment, the ultrasound diagnosis apparatus 100 may display a current state of contact between the probe 200 and the object, based on which the user enters a user input for a tilt direction and a tilt amount of the probe 200 via the input interface 170.

The ultrasound diagnosis apparatus 100 changes a tilt of the probe 200 based on the user input entered by the user in operation S860 (S870). According to an embodiment, a tilt direction and a tilt amount of the probe 200 may be determined based on a user input signal, and accordingly, a relative position of the probe 200 with respect to the object may be improved, and an improved ultrasound image may be obtained.

Figure 16:
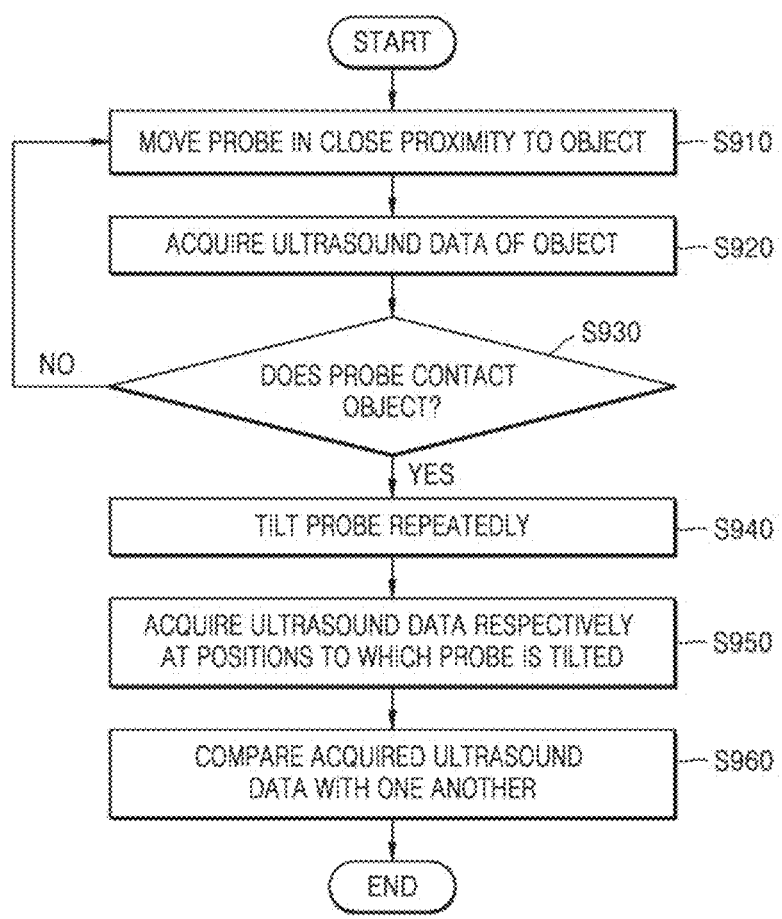
FIG. 16 is a flowchart of a method of operating an ultrasound diagnosis apparatus, according to an embodiment.

FIG. 16 is a flowchart of a method of operating the ultrasound diagnosis apparatus 100, according to an embodiment.

According to an embodiment, after displaying a visual indicator indicating the starting of tilting of the probe 200 in operation S840 of FIG. 8 when the probe 200 comes in contact with the object, the ultrasound diagnosis apparatus 100 may not determine whether the user input is entered in operation S860 but automatically perform tilting of the probe 200 in operation S940 for transmission and reception of ultrasound signals.

For example, the ultrasound diagnosis apparatus 100 may automatically tilt the probe 200 after determining whether the probe 200 and the object are brought into contact with each other in operation S930. According to an embodiment, as shown in FIGS. 5A through 5C and FIGS. 6A through 6C, the probe 200 may be tilted relative to the first X axis or the second Y axis, but a direction in which the probe 200 is tilted is not limited to the first X axis or the second Y axis. Although not shown in FIGS. 5A through 5C and FIGS. 6A through 6C, the probe 200 may rotate about the third Z axis. The probe 200 may be tilted or rotate at an angle that is less than or equal to 15° with respect to each axis, but embodiments are not limited thereto.

The ultrasound diagnosis apparatus 100 respectively acquires ultrasound data at positions to which the probe 200 is tilted. The probe 200 may respectively acquire, from positions to which the probe 200 is tilted, ultrasound data by transmitting ultrasound signals to the object and receiving ultrasound echo signals reflected from the object. By using the acquired ultrasound data, the first region 510 with respect to which ultrasound data is acquired and the second region 520 with respect to which ultrasound data is not acquired may be distinguished from each other in an ultrasound image.

The ultrasound diagnosis apparatus 100 compares the ultrasound data respectively acquired at the positions to which the probe 200 is tilted with one another (S960). The probe 200 may respectively acquire a plurality of pieces of ultrasound data from positions to which the probe 200 is tilted, and determine a tilt position at which the first region 510, with respect to which ultrasound data is acquired from among the plurality of pieces of ultrasound data, has a largest area. Thus, the ultrasound diagnosis apparatus 100 may automatically obtain a clearer image by holding the probe 200 steadily in the determined tilt position. According to the method, the ultrasound diagnosis apparatus 100 may obtain a relatively clear ultrasound image without requiring the user to adjust a tilt direction and a tilt amount of the probe 200 during measurement for obtaining an ultrasound image.

What is claimed is:

1. An ultrasound diagnosis apparatus comprising:
   a probe configured to transmit ultrasound signals to an object and receive ultrasound echo signals reflected from the object;
   a display configured to display a state of contact between the object and the probe; and
   a processor configured to:
      generate an ultrasound image using the ultrasound echo signals,
      distinguish a first region in which ultrasound data is obtained and a second region in which ultrasound data is not obtained in the ultrasound image,
      determine the state of contact between the object and the probe based on a ratio between the first region and the second region,
      control the display to output a first indicator that indicates tilting of the probe is starting based on the state of contact between the object and the probe, and
      control the display to output a second indicator including tilt information of the probe after the first indicator is output.

2. The ultrasound diagnosis apparatus of claim 1, further comprising an input interface configured to receive a user input for adjusting a tilt of the probe according to the second indicator,
   wherein the probe is configured to be controlled so as to be tilted according to the received user input.

3. The ultrasound diagnosis apparatus of claim 1, wherein the display further comprises an audio device, or a vibration device equipped with haptic functions.

4. The ultrasound diagnosis apparatus of claim 3, wherein the first indicator that indicates the tilting of the probe is starting is output as at least one from among an image, a text, an audio signal, and a vibration.

5. The ultrasound diagnosis apparatus of claim 3, wherein the second indicator is output as at least one of from among an image, a text, and an audio signal.

6. The ultrasound diagnosis apparatus of claim 1, wherein the processor is further configured to control the probe so as to be tilted at a specific angle, and control the probe to repeat an operation of transmitting the ultrasound signals, respectively at positions to which the probe is tilted, and control the probe to receive the ultrasound echo signals reflected from the object.

7. The ultrasound diagnosis apparatus of claim 1, wherein the probe is positioned at a distal end of the ultrasound diagnosis apparatus and is a transesophageal echocardiography (TEE) probe for insertion into a body cavity,
   the ultrasound diagnosis apparatus further comprising a neck assembly that is connected to the probe and configured to be bent.

8. A method of operating an ultrasound diagnosis apparatus, the method comprising:
   moving a probe in close proximity to an object;
   transmitting, by the probe, ultrasound signals to the object and receiving ultrasound echo signals reflected from the object;
   generating an ultrasound image using the ultrasound echo signals;
   distinguishing a first region in which ultrasound data is obtained and a second region in which ultrasound data is not obtained in the ultrasound image;
   determining a state of contact between the object and the probe based on a ratio between the first region and the second region;
   outputting, by a display, a first indicator that indicates tilting of the probe is starting based on the state of contact between the object and the probe; and
   outputting, by the display, a second indicator including tilt information of the probe after the first indicator is output.

9. The method of claim 8, further comprising:
   receiving a user input for adjusting a tilt of the probe according to the tilt information of the probe, and adjusting the tilt of the probe based on the user input.

10. The method of claim 8, wherein the first indicator that indicates tilting of the probe is starting is output as at least one from among an image, a text, an audio signal, and a vibration.

11. The method of claim 9, wherein the second indicator is output as at least one from among an image, a text, and an audio signal.

12. The method of claim 8, wherein, when the ultrasound diagnosis apparatus includes a transesophageal echocardiography (TEE) probe for insertion into a body cavity as the probe, and the moving of the probe in close proximity to the object comprises inserting the probe into the body cavity and bending a neck assembly connected to the probe positioned at a distal end of the ultrasound diagnosis apparatus.

* * * * *